US009616022B1

(12) United States Patent
Roy et al.

(10) Patent No.: US 9,616,022 B1
(45) Date of Patent: Apr. 11, 2017

(54) NANODIAMOND COMPOSITIONS AND THEIR USE FOR DRUG DELIVERY

(71) Applicants: Upal Roy, Harrisonburg, VA (US);
Vadym Drozd, Miami, FL (US);
Madhavan Nair, Miami, FL (US);
Surendra K. Saxena, Miami, FL (US);
Andriy Durygin, Sweetwater, FL (US)

(72) Inventors: Upal Roy, Harrisonburg, VA (US);
Vadym Drozd, Miami, FL (US);
Madhavan Nair, Miami, FL (US);
Surendra K. Saxena, Miami, FL (US);
Andriy Durygin, Sweetwater, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/204,652

(22) Filed: Jul. 7, 2016

(51) Int. Cl.
*A61K 9/16* (2006.01)
*A61K 31/536* (2006.01)

(52) U.S. Cl.
CPC ............ *A61K 9/1611* (2013.01); *A61K 9/167* (2013.01); *A61K 31/536* (2013.01); *Y10S 514/934* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| 2008/0081074 A1* | 4/2008 | Gu ...................... A61K 9/5153 424/489 |
| 2010/0040672 A1* | 2/2010 | Ho ...................... A61K 9/7007 424/443 |
| 2010/0129457 A1* | 5/2010 | Razavi .................... B82Y 5/00 424/489 |

OTHER PUBLICATIONS

VN Mochalin, A Pentecost, X-M Li, I Neitzel, M Nelson, C Wei, T He, F Guo, Y Gogotsi. "Adsorption of Drugs on Nanodiamond: Toward Development of a Drug Delivery Platform." Molecular Pharmaceutics, vol. 10, 2013, pp. 3728-3735.*
A Pusuluri, A Kadam. "Nanodiamonds: En Route for Next Big Leap—'Theragnostics'." Pharma Utility, vol. 6 Issue 3, 2012, 10 printed pages.*

(Continued)

*Primary Examiner* — Isaac Shomer
(74) *Attorney, Agent, or Firm* — Saliwanchik, Lloyd & Eisenschenk

(57) ABSTRACT

The subject invention provides materials and methods for treating diseases affecting the central nervous system (CNS) and/or other viral reservoir organs utilizing nanoscopic diamond particles, i.e., nanodiamonds (ND), loaded with therapeutic agents of interests. In one aspect, the subject invention provides a composition for treating a subject's brain and/or other organs acting as viral reservoirs, the composition comprising a plurality of ND particles measuring less than 10 nm in size, wherein the ND particles are loaded with at least one therapeutic agent of interest. In another aspect, the subject invention provides methods of treating disorders affecting the CNS such as, for example, the brain and other viral reservoir organs such as, for (Continued)

example, lymph nodes and gut-associated lymphoid tissues (GALT), utilizing the drug delivery system comprising a plurality of ND particles as provided herein.

**15 Claims, 11 Drawing Sheets
(10 of 11 Drawing Sheet(s) Filed in Color)**

(56) References Cited

OTHER PUBLICATIONS

T Wills, V Vega. "Elvitegravir: a once-daily inhibitor of HIV-1 integrase." Expert Opinion on Investigational Drugs, vol. 21(3), 2012, pp. 395-401.*
WA Banks, N Ercal, TO Price. "The Blood-Brain Barrier in NeuroAIDS." Current HIV Research, vol. 4 No. 3, 2006, pp. 1-8.*
CAS Registry Record for Efavirenz (CAS # 154598-52-4), Entered STN Apr. 26, 1994, 4 printed pages.*

* cited by examiner

| Genes | Fold Up- or Down-Regulation Nanodiamond (Unmodified) |
|---|---|
| CEBPD[1] | 3.25 |
| EGR3[1] | 4.08 |
| GRIN1[2] | 4.03 |
| GRM8[3] | -3.16 |
| HOMER1[1] | -4.00 |
| IGF1[4] | -4.86 |

FIG. 5C

NANODIAMOND COMPOSITIONS AND THEIR USE FOR DRUG DELIVERY

BACKGROUND OF INVENTION

Human immunodeficiency virus type 1 (HIV-1) remains one of the leading causes of death worldwide, principally in developing countries. Although therapeutic agents exist for the treatment of HIV-AIDS, drug-induced toxicities and pharmacokinetic limitations commonly result in poor compliance and disease related complications such as, for example, HIV-associated neurocognitive disorders (HAND).[2,4] HAND is one of the most common manifestations of HIV-1 pathogenesis that causes cognitive impairment and other CNS-related disorders.[5-9]

Even with the advent of combination antiretroviral therapy (cART), over 40% of HIV-1 infected patients experience neurological complications.[9] Moreover, rates of HAND are likely to rise in the coming years as anti-HIV-therapies continue to extend the lifespan of patients.

Major limitations of cART include, but are not limited to, complex dosing regimens, drug metabolism, and limited penetration into viral reservoir organs such as the CNS and the lymphoid tissues.[1,2]

For treating disorders such as HAND, delivery of therapeutic agents to the CNS remains a major challenge, primarily due to the ineffective transmigration of drugs through the blood-brain barrier (BBB).

In recent years, the advent of nanomedicine has stimulated the development of innovative systems for drug delivery. However, clinical success has been limited due to problems associated with biocompatibility, sustainability, and cytotoxicity of the drugs.

Nanodiamond (ND) is known to be a non-toxic, biocompatible, and chemically inert material when used under typical biological conditions. ND, being crystalline carbon particles with sizes on the order of nanometers (e.g. less than 10 nm), have demonstrated a unique ability to accommodate surface modifications. This is due to their surface activity and large surface area with respect to volume.

BRIEF SUMMARY

The subject invention provides materials and methods for treating and/or diagnosing a viral infection and/or diseases affecting the central nervous system (CNS) and/or other viral reservoir organs utilizing nanodiamond (ND) particles loaded with therapeutic and/or diagnostic agents.

In one aspect, the subject invention provides compositions for treating a subject's brain and/or other organs that act as a viral reservoir. In one embodiment, the composition comprises ND particles of less than 10 nm in size, wherein the ND particles are loaded with at least one therapeutic and/or diagnostic agent of interest.

In some embodiments, the surface of the ND particle can possess an electrostatic charge. In some embodiments, the surface of the ND particle can be chemically functionalized.

In preferred embodiments, unmodified ND particles provided herein can accommodate the adsorption of drugs capable of treating and/or diagnosing a disease such as, for example, neuro-AIDS (e.g., AIDS-related disorders of the CNS), brain tumors, and other neurodegenerative disorders (e.g., Parkinson's, Alzheimer's, post traumatic stress disorders (PTSd)).

In an exemplary embodiment, the therapeutic agent can be an anti-HIV drug such as, for example, Efavirenz (EFV).

In another aspect, the subject invention provides methods of treating disorders affecting the CNS (such as, for example, the brain) and other viral reservoir organs such as, for example, lymph nodes and gut-associated lymphoid tissues (GALT), wherein the method utilizes a drug delivery system comprising a plurality of ND particles as provided herein. In preferred embodiments, the method provided herein comprises delivering the ND composition across the blood-brain barrier (BBB).

BRIEF DESCRIPTION OF THE DRAWINGS

The file of this patent contains at least one drawing executed in color. Copies of this patent with color drawings(s) will be provided by the Patent and Trademark Office upon request and payment of the necessary fee.

FIGS. 1A-1C are TEM images of unmodified, —COOH modified, and —$NH_2$ modified ND, respectively. FIG. 1D is a graph showing the X-ray diffraction patterns of (a) unmodified ND in comparison with (b) —COOH modified and (c) —$NH_2$ modified ND in powder form. The reflecting atomic planes of diamond structure are denoted by Miller indices. FIG. 1E shows Raman spectra of (a) unmodified, (b) —COOH modified, and (c) —$NH_2$ modified ND.

FIG. 2A), which can be suspended in PBS (FIG. 2B), while FIG. 2C is an adsorption isotherm of EFV on ND. The dotted line shows the fit of experimental points by a Langmuir model.

FIGS. 5A-5D demonstrate human synaptic plasticity gene expression in ND-exposed SK-N-MCs. Out of the 84 genes analyzed that were related to synaptic plasticity of the neurons, only genes that were significantly up- (red) or down- (blue) regulated (≥±3 fold) are shown here (FIG. 5C). FIG. 5A is a 3D-profile of fold change of synaptic plasticity genes in ND exposed SK-N-MCs. FIG. 5B shows representative scatter plot analysis of the changes in synaptic plasticity gene expression in ND-exposed SK-N-MCs, wherein spots associated with individual human synaptic plasticity gene were collected and converted into log scale. The centerline indicates unchanged gene expression. The synaptic plasticity genes with expression levels higher or lower in treated neuronal cells than in the control cells are expected to produce dots that deviate from the centerline. The dots are allocated to positions that are above or below the +3 fold or −3 fold line when the differences are greater than 3 fold. FIG. 5C shows the human synaptic plasticity genes expression in ND-exposed SK-N-MCs (fold change). Out of the 84 genes analyzed, only genes significantly (±≥3 fold) dysregulated were shown in this table. FIG. 5D shows the gene-gene interaction network for human synaptic plasticity genes dysregulated in ND-exposed SK-N-MCs. It has been found that there were no gene-gene interactions among the dysregulated genes, as indicated by the absence of color-coded connections between various genes, suggesting that the ND has no immediate toxic effect on the synaptic plasticity genes of neuronal cells.

DETAILED DISCLOSURE

Figures 1A, 1B, 1C:
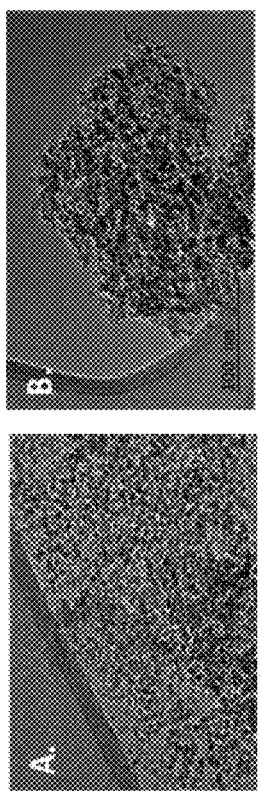
FIGS. 1A-1E show the results of various characterization techniques applied to the ND particles of the subject invention.

The subject invention provides materials and methods for treating and/or diagnosing diseases affecting the central nervous system (CNS) and/or other viral reservoir organs by utilizing nanodiamond (ND) particles loaded with therapeutic and/or diagnostic agents.

In one aspect, the subject invention provides a composition for treating a subject's brain and/or other organs that act as viral reservoirs. In one embodiment, the composition comprises a plurality of ND particles of less than 10 nm in size, wherein the ND particles are loaded with at least one therapeutic and/or diagnostic agent.

In some embodiments, the composition comprises nanodiamond (ND) particles that are chemically synthesized carbon nanoparticles that feature a diamond core. In certain embodiments, the surface of the ND particles comprises diamond or diamond-like carbons such as, for example, graphite, fullerene ($C_{60}$), layered shells, and/or amorphous carbon.

ND particles can be formed using a number of techniques such as, for example, pulsed laser ablation (PLA), shock wave synthesis, chemical vapor deposition (CVD), and the like. Commercially available ND particles are typically produced by impact events such as an explosion occurring over an extremely short period of time under high pressure and temperature conditions, e.g., over 20 GPa and 3000° C.

In preferred embodiments, PLA and arc-discharge are employed to create intense pressure and temperature shock conditions in a localized area to produce ND particles of desired sizes. The arc-discharge method produces ND particles by applying a direct-current arc voltage across two graphite electrodes immersed in an inert gas environment, creating a high temperature discharge between the two electrodes. The arc discharge vaporizes the surface of one of the electrodes and forms particle-shaped deposit on the other electrode. This highly non-equilibrium process has been shown to create nano-scale diamonds with advantageous surface properties. The PLA method can improve the ND production efficiency by replacing submerged carbon targets with organic liquids and by making a high-throughput fabrication system to obtain substantial quantities of ND particles.

In accordance with embodiments provided herein, the ND particles can be less than 100 nm in size and, preferably, have a narrow size distribution, e.g., 80% or more of the NDs having a diameter of from about 1 nm to about 10 nm (or within any of the other ranges set forth below). Suitable ND particles can have an average diameter from about 0.5 nm to about 50 nm. In some embodiments, the ND particles have an average diameter from about 1 nm to about 10 nm, preferably from about 3 nm to about 8 nm, and most preferably about 5 nm. Certain embodiments of the subject invention provide that the ND particles are small enough to penetrate the tight junctions of the BBB and subsequently migrate to selected treatment areas.

In certain embodiments, the surface of the ND particles can be electrostatically charged, facilitating the adsorption of various therapeutic and/or diagnostic agents having positive or negative charges. Optionally, the surface of the ND particles can be chemically modified with functionalities such as, for example, carboxylic acid, lactone, ketone, ether, hydroxyl, and/or amine. Furthermore, biological molecules such as, for example, amino acids, proteins, cells, hormones, vitamins, DNAs, siRNAs, antibodies, and RNAs, can be adsorbed or covalently attached to the ND particles' surfaces without altering their biological activities.

Advantageously, due to the electrostatic potential presented by the surface functionalities and the large surface area with respect to their volume, ND particles facilitate the adsorption of various functional groups and/or drug molecules to a greater extent when compared to other drug carriers.

In some embodiments, ND particles provided herein can accommodate the adsorption, or covalent bonding, of a drug capable of treating and/or diagnosing one or more diseases including, but not limited to, neuro-AIDS, brain tumors, other forms of cancer, Alzheimer's disease, Parkinson's disease, Huntington's disease, Traumatic brain injury (TBI) and other neurodegenerative disorders. In some embodiments, the CNS disease is caused by a latent HIV-1 infection. In preferred embodiments, ND particles can be loaded, via surface adsorption, with one or more anti-HIV drugs targeting the brain. The drugs may be, for example, an antiretroviral drug or a viral latency-breaking drug.

As disclosed herein, neuro-AIDS can be, for example, any of the AIDS-related disorders of the CNS caused by the HIV virus, by certain cancers, and by infections caused by bacteria, fungi, viruses, and the like, or by toxic effects of drugs used to treat such conditions. Non-limiting examples of neuro-AIDS include HIV-associated dementia (HAD), HIV-associated neurocognitive disorder (HAND), CNS lymphomas, Cryptococcal meningitis, and various psychological and neuropsychiatric disorders related to AIDS in the CNS.

In some embodiments, the drug is an antiretroviral drug selected from, for example, nucleoside reverse transcriptase inhibitors (NRTIs), non-nucleoside reverse transcriptase inhibitors (NNRTIs), nucleotide analog reverse transcriptase inhibitors (NtARTIs or NtRTIs), protease inhibitors (PIs), and integrase strand transfer inhibitors (INSTIs).

In some embodiments, the drug is a viral latency-activity drug selected from, for example, protein kinase C (PKC) agonists, histone deacetylase (HDAC) inhibitors, and nuclear factor kappa-light-chain-enhancer of activated B cells (NF-κB).

In an exemplary embodiment, the therapeutic agent is Efavirenz (EFV), a non-nucleoside reverse transcriptase inhibitor.

In some embodiments, the therapeutic or diagnostic agent, or "drug," delivered in the methods provided herein can be any natural or synthetic substance capable of being adsorbed onto, or forming chemical bonds with, the ND particles' surfaces and having a physiological or diagnostic effect when administered to an animal. The drug can be suitably employed in accordance with the invention with animals (subjects), particularly mammals including humans, domestic animals and farm animals. Thus, the animals include, for example, dogs, cats, cattle and pigs.

Drugs used in accordance with the subject invention can include those affecting, acting on, or being visualized at a desired target within, or on, the animal body, such as, for example, within the nervous system, including tumor tissue located therein. Specific examples of physiologically active drugs, which do not restrict the present invention, are therapeutic agents selected from the group consisting of: drugs acting at synaptic sites and neuroeffector junctional sites; general and local analgesics; hypnotics and sedatives; drugs for the treatment of psychiatric disorders such as depression and schizophrenia; anti-epileptics and anticonvulsants; drugs for the treatment of Parkinson's and Huntington's disease, aging and Alzheimer's disease; excitatory amino acid antagonists, neurotrophic factors and neuroregenerative agents; trophic factors; drugs aimed at the treatment of CNS trauma or stroke; drugs for the treatment of addiction and drug abuse; drugs for the treatment of bacterial, viral and/or microbial infections, such as influenza viral infections, HIV, herpes, chicken pox, and the like; antacids; anti-inflammatory drugs; immunosuppressive agents; anticancer drugs; hormones and hormone antagonists; heavy metals and heavy metal antagonists; antagonists for non-metallic toxic agents; cytostatic agents; diagnostic substances for use in nuclear medicine; immunoactive and immunoreactive agents; transmitters and their respective receptor agonists and receptor antagonists, their respective precursors and metabolites; transporter inhibitors; antibiotics; antispasmodics; antihistamines; antinauseants; relaxants; stimulants; sense and antisense oligonucleotides; cerebral dilators; psychotropics; antimanics; vascular dilators and constrictors; anti-hypertensives; drugs for migraine treatment; hypnotics, hyperglycemic and hypoglycemic agents; minerals and nutritional agents; anti-obesity drugs; anabolics; and anti-asthmatics.

In some embodiments, the ND particles-based drug formulation can be delivered as part of a composition that further comprises a physiologically acceptable carrier and/or diluent allowing the transport of the ND particles to the treatment areas after administration. The concentration of the ND particles in the carrier and/or diluent will vary depending on the nature of the therapeutic formulation and the desired effect thereof. As a practical matter, the plurality of ND particles is typically about 1 wt % to about 80 wt % of the drug formulation.

The carrier and/or diluent can be any medium by which the desired purpose is achieved and which does not affect the capability of the nanoparticles to travel to the desired target and to transport the therapeutic agent to this target treatment area for the desired pharmacological effect. Particularly, the carrier and/or diluent should not substantially deteriorate the pharmacological potency of the ND particles-based drug formulation and the capability of the formulation to be directed to a desired target within or on the mammalian body. Preferably, the carrier and/or diluent is selected from water, physiologically acceptable aqueous solutions containing salts and/or buffers and any other solution acceptable for administration to a subject. Such carriers and diluents are well known to a person skilled in this field and include, for example, distilled water, de-ionized water, pure or ultrapure water, saline, phosphate-buffered saline (PBS), and solutions containing usual buffers that are compatible with the other components of the materials and methods provided herein.

The administration of the ND particles-based formulation can be carried out in any desired manner or by any desired route of administration in order to achieve entry into the subject and transportation thereby to the treatment areas (e.g., the BBB). Administration can be by, for example, intravenous, oral, subcutaneous, intramuscular, intranasal, pulmonal, or rectal route. In preferred embodiments, the ND particles-based drug formulation suspended in solution is injected intravenously.

In some embodiments, the ND particles can be further modified to include a chemical tagging agent. The chemical tagging agent can be used to target the NDs to the site of interest in the subject brain. Examples include, but are not limited to, targeting antibodies, targeting ligands, aptamers, and antigens, such as cancer antigens. The chemical tagging agent can be attached to the surface of the NDs via, for example, an ionic or covalent bond.

Optionally, ND particles can be encapsulated in a coating layer comprising one or more polymers selected from glycerol monooleate (GMO), polyethylene glycol (PEG), and poly-L-lysine (PLL).

In another aspect, the subject invention provides methods of treating disorders affecting the brain utilizing the ND particles-based drug formulation. In a particular embodiment, the methods can be effective in treating latent HIV-1 infection in a subject's brain. In preferred embodiments, the methods provided herein comprise delivering the ND composition across the blood-brain barrier (BBB) and/or other tissues comprising cellular tight junctions similar to those of the BBB. In certain embodiments, the methods can also be used to treat other HIV-1 viral reservoir organs in addition to the brain, including, for example, the lymphoid tissues, bone marrow, genital tract, and gut-associated lymphoid tissues (GALT).

The BBB, a highly selective permeability barrier separating blood from brain extracellular fluid, comprises, inter alia, endothelial cells connected by tight junctions and human astrocytes. The term "tight junctions," as used herein, refers to multiprotein complexes formed between tightly joined cells that selectively regulate the diffusion of ions and water-soluble molecules through the paracellular pathway. Tight junctions are characterized by their high electrical resistance, approximately on the order of 1000 ohms-cm$^2$ (or higher) for structures such as the BBB. The ND particles-based drug formulation provided herein can also be used to treat other tissues comprising cellular tight junctions. The transmigrability of the subject ND particles-based formulation can be evaluated using an in-vitro BBB model comprising co-cultured primary human brain microvascular endothelial cells and astrocytes.

In an exemplary embodiment, unmodified and surface-modified ND particles-based formulations were examined, in-vitro, for their respective drug-loading capacity and cytotoxicity employing the anti-HIV drug EFV. The study demonstrated that unmodified nanodiamond (ND-EFV) particles are less toxic with significantly higher EFV loading capacity than both the —COOH modified (ND-COOH-EFV) and —$NH_2$ modified (ND-$NH_2$-EFV) ND particles. Further, ND-EFV particles also showed improved performance with respect to drug dissolution profile, therapeutic efficacy, and transmigration profile through the BBB when compared with the modified ND particles.

In some embodiments, the efficacy of the ND-EFV formulation can be further optimized by making a suspension of the formulation in a liquid. Being hydrophobic molecules, both EFV and ND were insoluble in water or phosphate buffer saline (PBS). In certain embodiments, solvents with ratios of PBS to DMSO (dimethyl sulfoxide) ranging from 1:1 to 1:9 were used to make the ND-EFV formulation soluble in physiological buffer media. In an exemplary embodiment, a PBS:DMSO ratio of approximately 1:9 was used for making a ND-EFV suspension, which was subsequently diluted in preparation to perform biological experiments.

Advantageously, the technology provided herein offers nontoxic, biocompatible ND-particles-based compositions capable of treating, for example, disorders affecting the brain and other HIV-1 viral reservoir organs, characterized in that the ND compositions can effectively transmigrate across the tight junctions of the BBB. Further, the increased drug-loading capacity attributed to ND particles' large surface area can lead to more sustained drug release profile and improved drug dosing regimens.

Following are examples that illustrate procedures for practicing the invention. These examples should not be construed as limiting.

Experiments were performed in multiple replicates and the data was presented as mean±SEM. The statistical significance of each experiment was analyzed by two-tailed paired t-test with GraphPad Prism software (GraphPad Prism software Inc. San Diego, Calif.) and a p value of ≤0.05 was considered as significant.

Materials and Instruments

Human neuroblastoma SK-N-MCs were obtained from ATCC (ATCC Cat. # HTB-10) and cultured in Eagle's minimum essential medium (MEM) (Cat. #30-2003) supplemented with fetal bovine serum to a final concentration of 10% (Cat. #30-2020) and 1% antibiotic/antimycotic solution (Sigma-Aldrich, St. Louis, Mo.). HIV-1 Ba-L (clade B) (Cat. #510) was obtained through AIDS Research and Reference Reagent Program, Division of AIDS, NIAID, NIH.

ND powder (3-6 nm, purity 97+%) was purchased from Nanostructured and Amorphous Materials Inc. (Garland, Tex., USA).

EFV drug powder and all other chemicals were obtained from Sigma-Aldrich (St. Louis, Mo., USA).

An Agilent 1200 HPLC system (Palo Alto, Calif.) coupled to an Applied Biosystem 4000 Q TRAP quadrupole linear ion trap hybrid mass spectrometer (Applied Biosystems/MDS Sciex, Foster City, Calif.) was used for drug analysis. The HPLC-MS/MS system is controlled by ChemStation and Analyst 1.4.2 software, respectively. All chromatographic separations were performed on an Agilent ZORBAX RP 18 column (3.5 m, 150 mm×0.5 mm) (Palo Alto, Calif.).

Amine-functionalized nanodiamond (ND-$NH_2$) was fabricated by procedures previously reported.[41] 50 mg ND powder was dispersed in absolute ethanol via sonication for 30 mins, and an excess amount of APTES solution was slowly dropped into the ND solution and stirred overnight at refluxing conditions on a water bath. The ND-$NH_2$ was centrifuged and subsequently washed with ethanol for at least 5 times, which was then dried at 80° C. under vacuum for 12 hrs. Oxidation (e.g. surface modification with carboxyl-groups) was performed at 425° C. in air for 2 hrs.[42]

EXAMPLE 1

Characterization of Nanodrug

Transmission Electron Microscopy (TEM)

TEM observation was helpful for determining the particle size, morphology and dispersity of the nanodrugs.

According to the TEM study (FIG. 1A-C), the ND particles have spherical morphology and average particles size in the range of 5-6 nm, which is close to vendor's specifications (3-5 nm). As should be expected, modifications of ND surface do not alter ND particles size, morphology, or crystal structure (FIG. 1D).

X-Ray Diffraction (XRD)

An X-ray diffraction study of ND was performed using a Bruker GADD/D8 X-Ray diffraction system with Apex Smart CCD and imaging plate detectors and direct-drive rotating anode. The MacSci rotating anode (molybdenum) operates at 50 kV voltages and 20 mA current. The 2D diffraction patterns obtained were integrated using Fit2D software.[43] This X-ray diffraction method was used for structural characterization of the materials and particle size measurements of the crystalline phases, and for estimating the degree of crystallinity.

Raman Spectroscopy Characterization

A continuous wave (CW) argon ion (Ar+) laser (model 177G02, Spectra Physics) of 514.5 nm in wavelength was used as a source of monochromatic radiation. Backscattered Raman spectra were collected by a high-throughput holographic imaging spectrograph (model HoloSpec f/1.8i, Kaiser Optical Systems) with volume transmission gratings, a holographic notch filter, and a thermoelectrically cooled charge-coupled device (CCD) detector (Andor Technology). The Raman system has spectral resolution of 4 $cm^{-1}$. The spectra were usually collected with 10 mins of exposure.

Figure 1E:
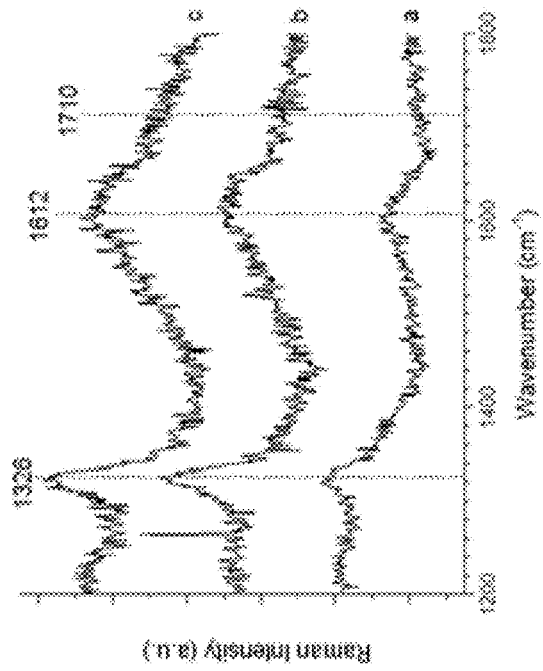
Figure 1D:
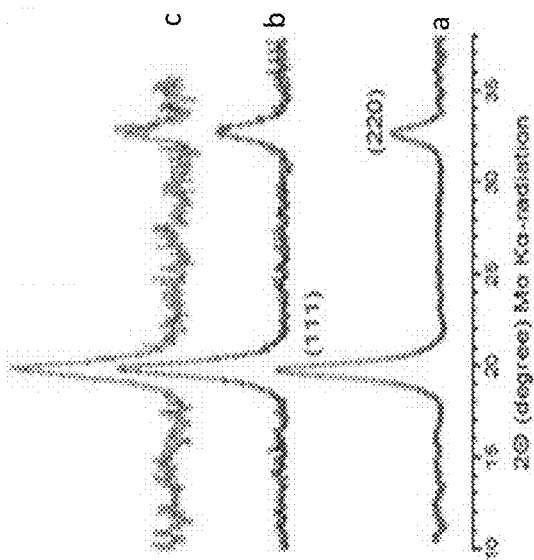

FIG. 1E shows Raman spectra of three ND that were used in this study: (a) unmodified, (b) —COOH modified, and (c) —NH2 modified ND. Raman spectra of all samples display the characteristic feature of the diamond phase (peak at 1326 $cm^{-1}$). According to Mochalin et al., (2009) a broad feature around 1612 $cm^{-1}$ can be assigned to graphitic carbon on ND surface (the G-band) with some contribution from hydroxyl groups which are chemo- or physisorbed onto the surface.[37] Following the surface modification, ND-COOH and ND-$NH_2$ particles were loaded with EFV as per the protocol provided herein.

EXAMPLE 2

Drug Absorption Study

In order to make an initial calibration curve, concentrations of 1:9 DMSO-water and EFV were made at 5, 40, 50, and 100 µg/mL from 10 mg/mL stock solution of EFV in a total volume of 2 mL for each concentration. The initial calibration curve was created using the absorbance values of the corresponding concentrations (250 nm). The dilutions were thoroughly mixed and the optical density (OD) value of each concentration was measured twice using Hitachi U-2910 Spectrophotometer (UV Spec.). 2 mg (0.002 g) of ND was then added to each glass tube. The tubes were then sonicated in ultrasonic bath for 2 mins. The tubes were then shaken at 25° C. and 190 rpm for approximately 24 hrs. The contents were then transferred to plastic microfuge tubes and mixed using Eppendorf Thermomixer for 1 hr at 600 rpm. The solutions were then centrifuged at 13,000 rpm for 1 hr. The supernatant of the solutions was removed (conservatively), leaving behind the ND pellet. The OD values of the supernatant for each concentration were measured using Hitachi U-2910. Based on the measured absorbance values before and after the adsorption, the concentrations of drug in the resulting solutions were calculated using the measured OD values.

Figure 2A:
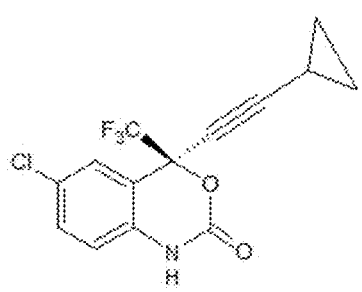
FIGS. 2A-2C show the chemical structure of Efavirenz (EFV.
Figure 2B:
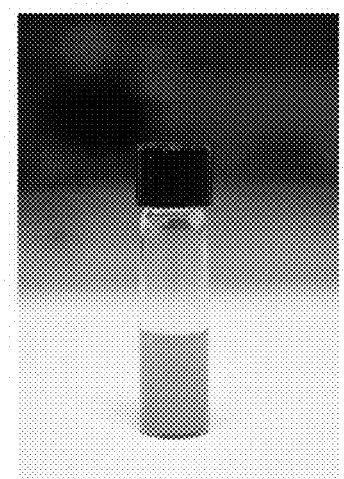
Figure 2C:
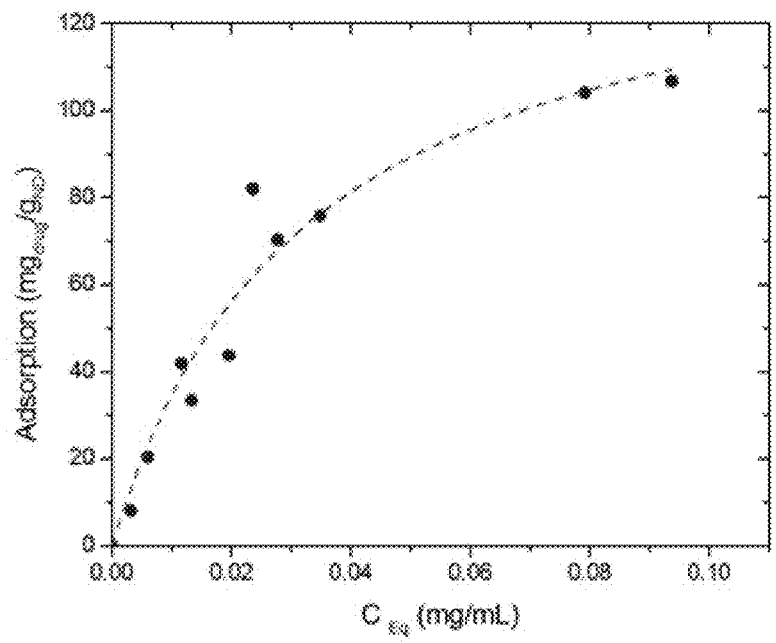

An adsorption isotherm of EFV on unmodified ND (milligrams of EFV absorbed per 1 g of ND) as a function of $C_{eq}$ (concentration of adsorbate in solution which is equilibrium with ND) is shown in FIG. 2C. Experimental points were fit by Langmuir adsorption model. This empirical model suggests homogeneous monolayer absorption of the drug on the surface of the adsorbent. Maximum adsorption capacity obtained from Langmuir isotherm was 161 mg EVF/1 g ND. KL constant that characterizes the bonding strength between the adsorbate (EFV) and the adsorbent (ND) was 23 mL/mg. In this regard, the relatively low value of KL suggested easy desorption of EFV from the ND.

Comparative analysis of EFV adsorption on ND, ND-COOH, and $ND-NH_2$, respectively, indicated that, with respect to time and increasing particle concentration, there is a clear distinction between the formulations. In this regard, unmodified ND and $ND-NH_2$ demonstrated similar EFV adsorption. ND-COOH, showed very low adsorption capacity for EFV.

EXAMPLE 3

Drug Analysis

HPLC Analysis

The EFV concentration in biological samples was quantitatively determined by a previously reported MRM method.[44] In brief, the tissue sample was homogenized with deionized $H_2O$ at a ratio of 1:2 (w/v). 1 mL of ice-cold ACN was added to a 100 µL homogenized tissue sample which spiked with 10 µL IS (2.0 g/mL lopinavir). The sample was then vortexed for 3 mins, shaken for 15 mins, and centrifuged at 16,000×g for 10 mins. The supernatant was aspirated, dried under vacuum at room temperature, and dissolved in 100 µL 50% MeOH aqueous solvent. Before injection, the sample was centrifuged for 10 mins at 16,000 g, and 8 µL of supernatant was injected into the HPLC-MS/MS system for analysis. For all samples, the final concentration of IS was 200 ng/mL. Linearity of the method (in the range of 0.2-1000 ng/mL) was confirmed by preparing 3 standard curves on 3 different days.

Dissolution Study

ND-EFV was tested for long term sustained release capacity in physiological buffer media. Briefly, a solution of ND-EFV nanoparticles (0.5 mL, concentration: 2 mg/20 mg ratio of EFV drug/ND) was placed into a dialysis bag (molecular cutoff: 6 kDa), sealed, and put into a tube filled with 30-40 mL dissolution solution (composition: 0.1% Tween 20 aqueous solution). Dispersion of the ND-EFV in PBS (pH 7.4) was placed in the dialysis bag (D-bag) (Pur-A-Lyzer Maxi Dialysis Kit, SIGMA) and dialyzed against the respective buffer solution at 37° C. at a speed of 150 rpm. At each time point (30 min, day-1, day-5 and day-14), 100 µL of solution was taken out from the tank and same amount of fresh buffer was replenished. The free EFV release study was also measured in similar conditions simultaneously. Final drug concentrations of the collected samples were determined by HPLC in the above mentioned fashion.

Figure 6:
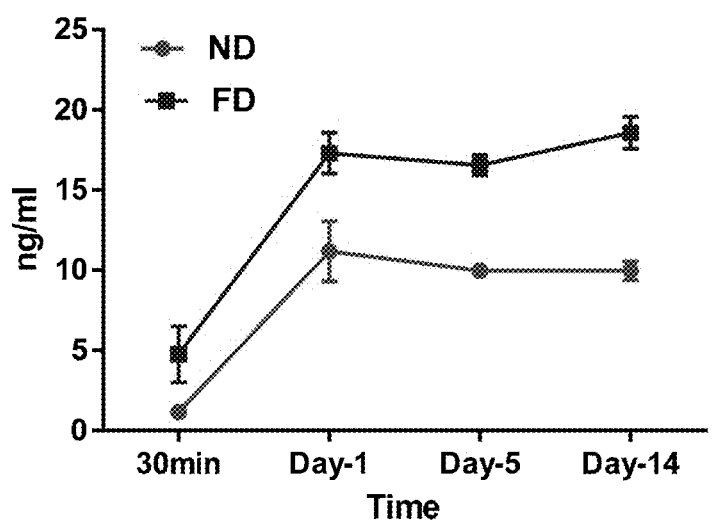
FIG. 6 shows the results of the drug dissolution study of an ND-based nanodrug formulation ("ND") in comparison to free drug formulation ("FD"). The released drug outside of the dialysis bag was measured from 30 mins up to Day 14 by HPLC. The data shown is an average of four different experiments ($p<0.05$).

The sustained drug released profile of the ND-EFV formulation was determined in PBS using equilibrium dialysis. The released drugs outside the dialysis bag were sampled at different time intervals (from 30 mins up to 14 days) and measured by high performance liquid chromatography (HPLC). As a positive control, equal amounts of free drug were introduced directly to the in-vitro PBS separately. Results were expressed as ng/mL of drug released from the ND relative to the initial drug loading (FIG. 6). Compared to the free drug (blue), ND-EFV (green) showed sustained drug release characteristics indicating improved pharmacokinetics of ND-EFV in-vitro. This observation suggests potential in-vivo drug release pattern in which a free drug will immediately be released and metabolized. Consequently, the ND-EFV sustained release pattern will aid drug delivery process in the CNS where slow release of drug is crucial for viral reservoir reduction.

EXAMPLE 4

Human Synaptic Plasticity $RT^2$ Profile PCR Array

Synaptic plasticity gene expression profiling was done in SK-N-MC control (untreated) cells and ND-EFV treated cells using 96 well format $RT^2$ Profile PCR Array human Synaptic Plasticity kit (SABiosciences, Cat. # PAHS-126A-2) using Stratagene Mx3000p qRTPCR instrument. This test included 84 diverse genes important in human synaptic plasticity, including Immediate-Early Response (n=30), Late Response (n=2), Long Term Potentiation (n=28), Long Term Depression (n=21), Cell Adhesion (n=9), Extracellular Matrix & Proteolytic Processing (n=5), CREB Cofactors (n=10), Neuronal Receptors (n=19), Postsynaptic Density (n=15), as well as other genes involved in the synaptic plasticity (n=2). Relative abundance of each mRNA species was assessed using $RT^2$ SYBR Green/ROX PCR Master mix (SABiosciences, Cat #330520) and aliquoted in equal volumes (25 µL) to each well of the real-time PCR arrays. The real-time PCR cycling program (as indicated by the manufacturer) was run on a Stratagene Mx3000p qRT-PCR thermal cycler. The threshold cycle (Ct) of each gene was determined by using the Stratagene MaxPro software. CT data was uploaded into the data analysis template on the manufacturer's website. The relative expression of each gene in each ND-EFV treated group was compared with the expression in control cells and it was calculated on the website using the ΔΔCT method with five housekeeping genes as controls. Controls were also included on each array for genomic DNA contamination, RNA quality, and general PCR performance.

When comparing the 84 human synaptic plasticity genes to the untreated control cells (FIGS. 5A-5D), significant downregulation was observed in GRM8 (3 fold), HOMER1 (4 fold), and IGF1 (4.8 fold) and significant upregulation was observed in CEBPD, EGR3 and GRIN1 was observed in ND-EFV treated neuronal cells. Nonetheless, results shown in FIGS. 5A-5D also illustrate that there was no connection between upregulated or downregulated genes, and thus, no potential deleterious effect on neuronal plasticity was observed. These results indicated that ND-EFV has no toxic effect on neuronal plasticity of human neurons, facilitating the long-term use of ND-EFV without any side effects to neurons.

EXAMPLE 5

Reactive Oxygen Species (ROS) Assay

ROS productions in SK-N-MCs following exposure to different concentrations of ND, ND-COOH, and ND-$NH_2$, respectively, were detected using dichlorofluorescein diacetate assay (DCF-DA; Molecular Probes, Eugene, Oreg.) as per previous published protocol.[45] Cells were cultured in 96-well plates (100,000 cells/well) overnight to allow 70% confluence. On the next day, cells were treated with different concentrations of ND, ND-COOH, and ND-$NH_2$ (10, 20, 40, 80, 100, 200, 400, 800, and 1000 µg/mL), respectively, for 24 hrs. On the following day, cells were washed and pretreated with antioxidant catalase (0.001 mg) for 2 hrs. Next, the cells were treated with DCF-DA (100 µM) for 1 hr at 37° C., and finally, the cells were read in a BioTek Synergy HT microplate reader (excitation 485 nm and emission 528 nm; BioTek, Winooski, Vt.). Cells treated with $H_2O_2$ (50 µM) for 2 hrs were included as the positive control.

Figure 3:
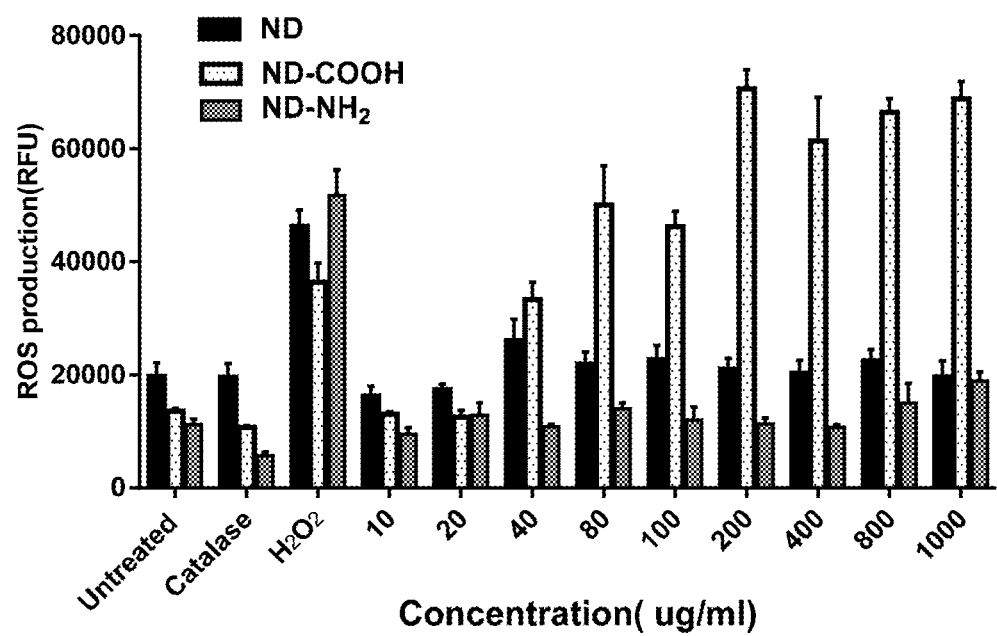
FIG. 3 shows the effect of unmodified NDs, —COOH modified NDs, and —$NH_2$ modified ND on ROS production of SK-N-MCs. The SK-N-MCs were exposed to different concentrations (10-1000 µg/mL) of ND, with or without chemical modification, for 24 hrs, respectively. At the end of the incubation, ROS production was measured in treated cells compared to untreated cells. The ROS production was measured in terms of mean±SE relative fluorescence units (RFU) values off previous independent experiments.
Figure 4:
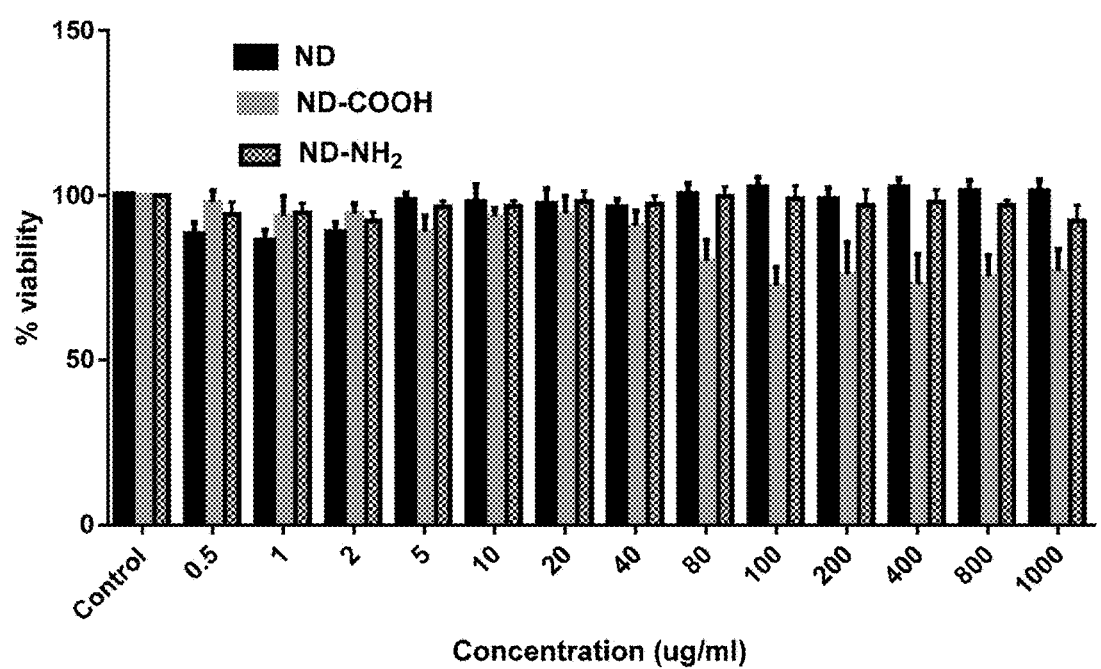
FIG. 4 compares the cytotoxicity of unmodified ND, —COOH modified ND, and —$NH_2$ modified ND on SK-N-MCs. The cells were treated with a range of concentrations (0.5-1000 µg/mL) of the three ND formulations for 24 hrs. After incubation, MTS assays were performed and optical density (OD) was measured at 490 nm. Graphical representation was made in terms of % survival of cells at different concentrations of the ND formulations corresponding to their OD values. Untreated cells (control) were considered as 100% viability and % survival was monitored based on control.
Figure 5A:
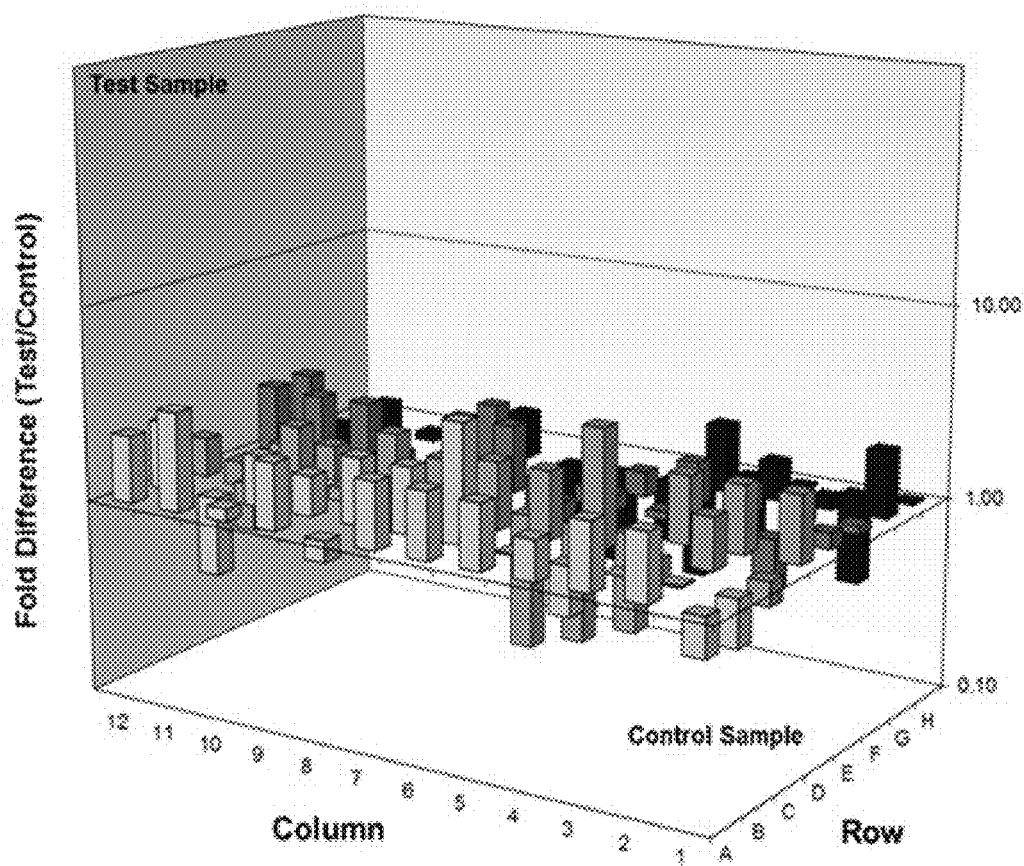
Figure 5B:
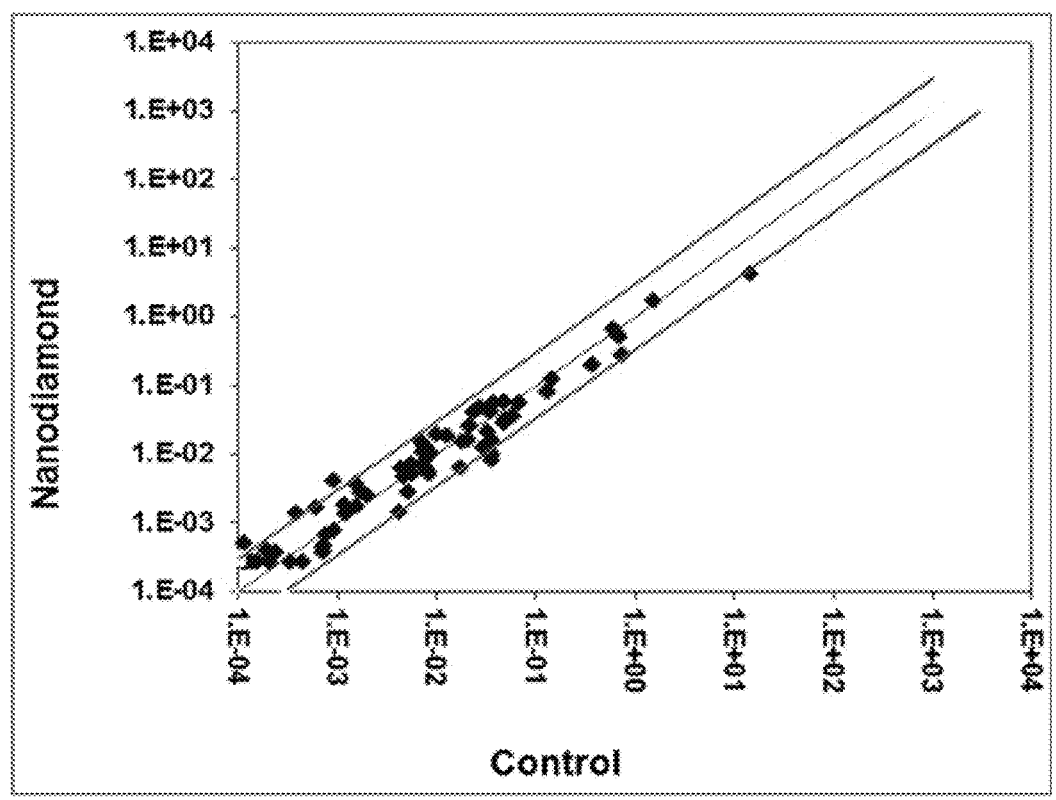
Figure 5D:
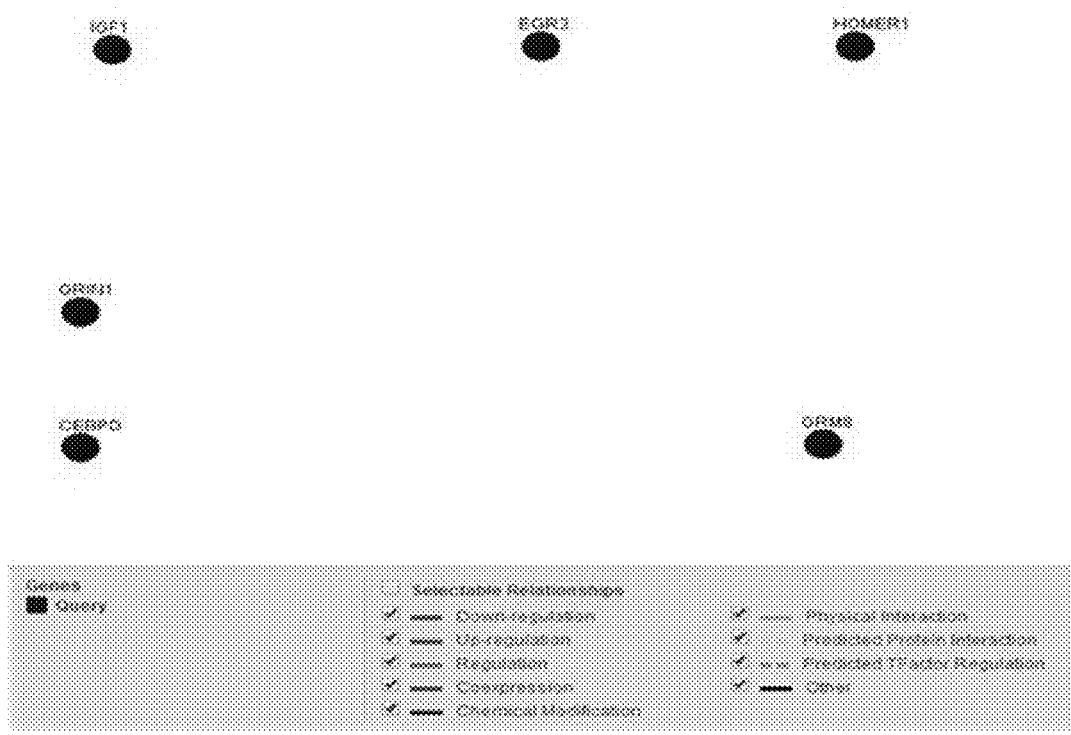

As shown in the FIG. 3, ND, ND-COOH, and ND-$NH_2$ had varied effect on SK-N-MC with respect to their ROS production. Compared to antioxidant (catalase) and the positive control ($H_2O_2$), ND and ND-$NH_2$ treatment did not exhibit any significant changes in the ROS production at the different concentrations tested in this study. On the other hand, ND-COOH treated cells showed significantly higher ROS release in all tested concentrations on SK-N-MC, indicating overall cytotoxicity.

Based on the ROS assay, it was observed that ND-COOH formulation was substantially more toxic to neuronal cells compared to ND and ND-$NH_2$.

EXAMPLE 6

Cellular Toxicity of Nanodrug

Cytotoxicity of ND, ND-COOH, and ND-$NH_2$ on SK-N-MCs were determined via an MTS assay (G3582, Promega, Madison, Wis., USA,).[46]

Cells were pre-incubated in 96-well plates with SK-N-MCs and then treated with various concentrations of nanodrug (control, 0.5, 1, 2, 5, 10, 20, 40, 80, 100, 200, 400, 800 and 1000 µg/mL) respectively for 24 hrs at 37° C. After treatment, cells were washed and incubated with fresh respective growth medium. Cells were further incubated with 20 µL of MTS reagent (CellTiter 96® AQueous One Solution, Madison, Wis., USA) in complete 100 µL cell media for 1 hr at 37° C. Following incubation, an absorbance at 490 nm was measured using the BioTek plate reader (BioTek, Winooski, Vt., USA). Untreated cells incubated with fresh media were used as a negative control. All measurements were taken eight times. The net absorbance (A) was taken as an index of cell viability. The cell viability was calculated as sample/control×100%. The nanoformulations that did not cause more than 10% loss in cell viability after at least 24 hrs of exposure were considered nontoxic.

FIGS. 5A-5D show that the SK-N-MC viability did not change significantly with increasing concentrations of ND and ND-$NH_2$ when compared to the control. However, the ND-COOH treatment had a significant effect on reducing cell viability at concentrations higher than 40 g/mL.

Considering the chemical characterization, cytotoxicity, and ROS assay results, it was observed that ND and ND-$NH_2$ were more biocompatible and less toxic to neuronal cells than the ND-COOH treatment.

Further, a comparative analysis of ND, ND-COOH, and ND-$NH_2$ formulations showed ND-COOH to be relatively less efficient in EFV loading and more toxic to the neuronal cells. On the other hand, ND and ND-$NH_2$ showed a similar capacity for drug loading and were nontoxic to cells. As ND-$NH_2$ possessed a similar drug loading capacity and relatively similar biocompatibility as ND, unmodified ND was selected for further in-vitro characterization.

EXAMPLE 7

Drug Delivery Through the BBB

Primary human brain microvascular endothelial cells (HBMVEC) and astrocytes were obtained from Sciencell Research Laboratories, Carlsbad, Calif. An in-vitro BBB model was established in trans-well plate as per published protocol.[47,48] HBMVECs were inoculated at the upper side of 0.4-µm pore size PTFE membrane tissue culture inserts (Corning, N.Y.) at initial concentration of 104 cells/well. A confluent layer of human astrocytes was grown on the lower side of the membrane. After incubation, integrity of the BBB was measured with transendothelial electrical resistance (TEER) using Millicell ERS microelectrodes (Millipore). For the drug delivery study, HBMVEC were allowed to grow up to 70% confluency and then ND-EFV (40 µg/mL) was introduced to the upper side of trans-well insert. Afterwards, cell media was collected at different time points (30 mins, 1 hr, Day 1, and Day 2) from the lower chamber and the upper chamber was replenished with fresh media. The drug content of the collected medium was measured through HPLC as mentioned above. Simultaneously, unformulated drug was also introduced in a similar setup and monitored for drug release with respect to the same time period.

Figure 7:
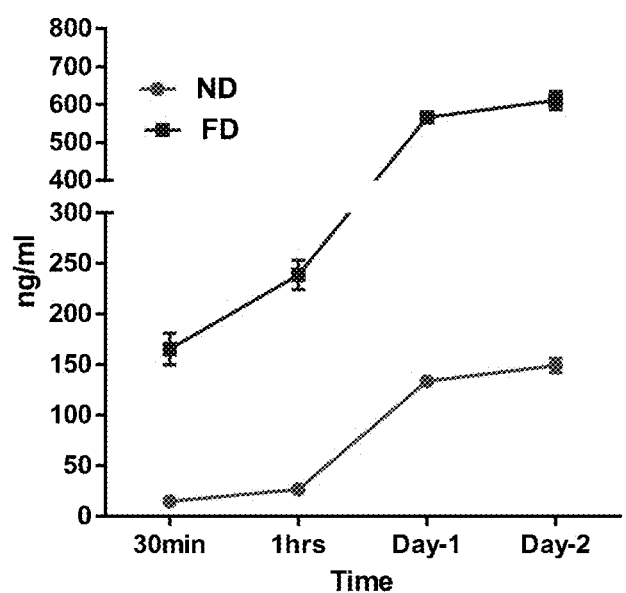
FIG. 7 displays the drug delivery profile of the ND-EFV nanodrug through an in-vitro BBB model. ND-EFV ("ND") and unformulated EFV ("FD") (40 μg/mL) were introduced separately to the upper chamber of the BBB model. EFV drug release was observed at different time points (30 min-Day 2) at the lower chamber of the BBB model. A comparative analysis of sustained drug release from ND-EFV versus unformulated EFV through BBB was monitored in terms of the drug content in the media with respect to time. Each drug release study was done in three replicates and data were represented with the statistical significance ($p \leq 0.0001$).

Although the drug release study showed that unformulated EFV possesses a very robust drug release on the CNS side of the BBB model (FIG. 7), the ND-EFV demonstrated significantly slower release of EFV compared to unformulated EFV.

Thus, ND-EFV is advantageous for anti-HIV-1 drug delivery to the CNS due to its ability to cross BBB and extend the circulation time of EFV in the CNS.

EXAMPLE 8

Therapeutic Efficacy

ND-EFV was investigated for anti-HIV-1 efficacy in primary human macrophage. Human peripheral blood mononuclear cells (PBMCs) were isolated from a healthy subject and differentiated into macrophages as previously published.[45] PBMCs were isolated with Ficoll-Hypaque (Pharmacia) gradient and cells were incubated for differentiation for 7 days in the presence of human macrophage colony stimulating factor (MCSF, Sigma) to macrophages. Following incubation, macrophages were infected with HIV-1 1Ba-L (NIH AIDS research and reference reagent program Cat#510) (100 ng/mL) for 24 hrs. On the next day, cells were washed to get rid of any unattached virus and fresh media was added. At the same time, 40 µg/mL of ND-EFV and unformulated EFV was added to these cells in two different setups. The HIV-1 infected macrophages served as a positive control. The ND-EFV/EFV treated cells were monitored for up to 10 days along with the infected control cells. The cell supernatant was collected at Day 0, 1, 2, 3, 5, and 7 post-treatment. The viral p24 level in the supernatant was measured with p24 ELISA assay (Cat. #0801200, Zeptometrix, USA). The p24 level at different time points provided the level of viral inhibition caused by ND-EFV and EFV. The p24 level at the culture supernatant will be inversely proportional to therapeutic efficacy of ND-EFV.

HIV-1 p24 level at cell supernatant of drug-treated cells indicated a significant difference on viral inhibition by unformulated EFV and ND-EFV. The effect of ND-EFV on HIV-1 replication was observed to be robustly effective and sustained over a period of 7 days. In contrast, the unformulated EFV could control viral replication up to Day 5, and p24 returned to untreated levels thereafter. This indicates the decreasing efficacy of unformulated EFV on HIV-1 replication for an extended period of time. Infected and untreated macrophages were kept as positive controls.

Figure 8:
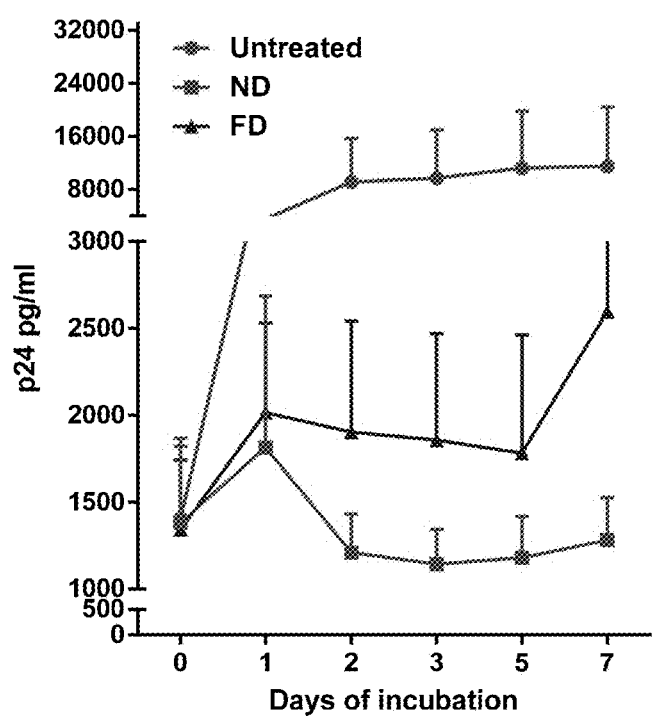
FIG. 8 demonstrates the therapeutic efficacy of ND-EFV on HIV-1-infected PBMCs. HIV-infected PBMCs were exposed to ND-EFV (40 μg/mL) at Day 0, following which the replication of HIV was monitored under three different conditions. The HIV-infected cells that were kept untreated served as the positive control ("Untreated"). Another batch of HIV-infected cells were treated with unformulated EFV (40 g/mL) and served as the reference ("FD"). The ND-EFV treated cells were considered as the test ("ND"). In all three sets of treatments, p24 levels were measured at a different time interval to measure HIV replication treatment. Statistical significance was calculated with respect to p values ($p \leq 0.0001$).

FIG. 8 confirms the efficacy of ND-EFV compared to unformulated EFV. This further demonstrates the advantages of using ND-EFV for targeted drug delivery towards the CNS.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

As used in the specification and appended claims, directional terms, such as "top," "bottom," "up," "down," "upper," "lower," "proximal," "distal," and the like are used herein solely to indicate relative directions and are not otherwise intended to limit the scope of the invention or claims.

All patents, patent applications, provisional applications, and publications referred to or cited herein are incorporated by reference in their entirety, including all figures and tables, to the extent they are not inconsistent with the explicit teachings of this specification.

REFERENCES

1. Bogich T L, Chunara R, Scales D, et al. Preventing pandemics via international development: a systems approach. PLoS medicine. 2012; 9(12):e1001354.
2. Gisslen M, Rosengren L, Hagberg L, Deeks S G, Price R W. Cerebrospinal fluid signs of neuronal damage after antiretroviral treatment interruption in HIV-1 infection. AIDS research and therapy. Aug. 18, 2005; 2:6.
3. Aceti A, Gianserra L, Lambiase L, Pennica A, Teti E. Pharmacogenetics as a tool to tailor antiretroviral therapy: A review. World Journal of Virology. 2015; 4(3):198-208.
4. Mellgren A, Antinori A, Cinque P, et al. Cerebrospinal fluid HIV-1 infection usually responds well to antiretroviral treatment. Antiviral therapy. 2005; 10(6):701-707.
5. AaMF B. Psychological manifestations. In: Witzburg HLaRA, ed. HIV Infection: A Clinical Manual Boston: Little, Brown and Company; 1993: 219-229.
6. Cysique L A J, Maruff P, Darby D, Brew B J. The assessment of cognitive function in advanced HIV-1 infection and AIDS dementia complex using a new computerised cognitive test battery. Archives of Clinical Neuropsychology. 2//2006; 21(2):185-194.
7. Sacktor N, McArthur J. Prospects for therapy of HIV-associated neurologic diseases. Journal of neurovirology. April 1997; 3(2):89-101.
8. Schifitto G, Kieburtz K, McDermott M P, et al. Clinical trials in HIV-associated cognitive impairment: cognitive and functional outcomes. Neurology. Feb. 13, 2001; 56(3):415-418.
9. Sidtis J J, Gatsonis C, Price R W, et al. Zidovudine treatment of the AIDS dementia complex: results of a placebo-controlled trial. AIDS Clinical Trials Group. Annals of neurology. April 1993; 33(4):343-349.
10. Chun T W, Fauci A S. HIV reservoirs: pathogenesis and obstacles to viral eradication and cure. Aids. Jun. 19, 2012; 26(10):1261-1268.
11. Roy U, Rodriguez J, Barber P, das Neves J, Sarmento B, Nair M. The potential of HIV-1 nanotherapeutics: from in vitro studies to clinical trials. Nanomedicine. December 2015; 10(24):3597-3609.
12. Mochalin V N, Shenderova O, Ho D, Gogotsi Y. The properties and applications of nanodiamonds. Nature nanotechnology. January 2012; 7(1):11-23.
13. Laura K. Moore M G, Edward K. Chow, and Dean Ho. Diamond-Based Nanomedicine: Enhanced Drug Delivery and Imaging. Disruptive Science and Technology. 2012; 1(1):54-61.
14. Man H B, Ho D. Nanodiamonds as Platforms for Biology and Medicine. Journal of Laboratory Automation. Feb. 1, 2013 2013; 18(1):12-18.
15. Kuang-Kai L, Chia-Liang C, Chia-Ching C, Jui I C. Biocompatible and detectable carboxylated nanodiamond on human cell. Nanotechnology. 2007; 18(32):325102.
16. Schrand A M, Huang H, Carlson C, et al. Are diamond nanoparticles cytotoxic? The journal of physical chemistry. B. Jan. 11, 2007; 111(1):2-7.
17. Krueger A, Lang D. Functionality is Key: Recent Progress in the Surface Modification of Nanodiamond. Advanced Functional Materials. 2012; 22(5):890-906.
18. Huang H, Pierstorff E, Osawa E, Ho D. Active nanodiamond hydrogels for chemotherapeutic delivery. Nano letters. November 2007; 7(11):3305-3314.
19. Villerbu N, Gaben A M, Redeuilh G, Mester J. Cellular effects of purvalanol A: a specific inhibitor of cyclin-dependent kinase activities. International journal of cancer. Feb. 20, 2002; 97(6):761-769.
20. May F E, Westley B R. Effects of tamoxifen and 4-hydroxytamoxifen on the pNR-1 and pNR-2 estrogen-regulated RNAs in human breast cancer cells. The Journal of biological chemistry. Nov. 25, 1987; 262(33):15894-15899.
21. Rouanet P, Linares-Cruz G, Dravet F, et al. Neoadjuvant percutaneous 4-hydroxytamoxifen decreases breast tumoral cell proliferation: a prospective controlled randomized study comparing three doses of 4-hydroxytamoxifen gel to oral tamoxifen. Journal of clinical oncology: official journal of the American Society of Clinical Oncology. May 1, 2005; 23(13):2980-2987.
22. Huang H, Chen M, Bruno P, et al. Ultrananocrystalline diamond thin films functionalized with therapeutically 23. Laccrda L, Bianco A, Prato M, Kostarelos K. Carbon nanotubes as nanomedicines: From toxicology to pharmacology. Advanced Drug Delivery Reviews. Dec. 1, 2006; 58(14):1460-1470.
24. Liu Z, Robinson J T, Sun X, Dai H. PEGylated nanographene oxide for delivery of water-insoluble cancer drugs. Journal of the American Chemical Society. Aug. 20, 2008; 130(33):10876-10877.
25. Kircheis R, Wightman L, Wagner E. Design and gene delivery activity of modified polyethyleneimines. Adv Drug Deliv Rev. Dec. 31, 2001; 53(3):341-358.
26. Yen A, Zhang K, Daneshgaran G, Kim H J, Ho D. A Chemopreventive Nanodiamond Platform for Oral Cancer Treatment. Journal of the California Dental Association. February 2016; 44(2):121-127.
27. Reina G O S, Cairone C, Tamburri E, Lenti S, Cianchetta I, Rossi M, Terranova M L. Rhodamine/Nanodiamond as a System Model for Drug Carrier. J Nanosci Nanotechnol. 2015; 15(2):1022-1029.
28. Lai L, Barnard A S. Functionalized Nanodiamonds for Biological and Medical Applications. Journal of nanoscience and nanotechnology. February 2015; 15(2):989-999.
29. Kim H, Man H B, Saha B, et al. Multiscale Simulation as a Framework for the Enhanced Design of Nanodiamond-Polyethylenimine-based Gene Delivery. The journal of physical chemistry letters. Dec. 4, 2012; 3(24):3791-3797.
30. Shimkunas R A, Robinson E, Lam R, et al. Nanodiamond-insulin complexes as pH-dependent protein delivery vehicles. Biomaterials. 10//2009; 30(29):5720-5728.
31. Purtov K V, Petunin A I, Burov A E, Puzyr A P, Bondar V S. Nanodiamonds as Carriers for Address Delivery of Biologically Active Substances. Nanoscale Research Letters. 2010; 5(3):631-636.
32. Jarre G, Heyer S, Memmel E, Meinhardt T, Krueger A. Synthesis of nanodiamond derivatives carrying amino functions and quantification by a modified Kaiser test. Beilstein journal of organic chemistry. 2014; 10:2729-2737.
33. Dhoro M, Zvada S, Ngara B, et al. CYP2B6*6, CYP2B6*18, Body weight and sex are predictors of efavirenz pharmacokinetics and treatment response: population pharmacokinetic modeling in an HIV/AIDS and TB cohort in Zimbabwe. BMC pharmacology & toxicology. 2015; 16:4.
34. Olagunju A, Bolaji O, Amara A, et al. Breast milk pharmacokinetics of efavirenz and breastfed infants' exposure in genetically defined subgroups of mother-infant pairs: an observational study. Clinical infectious diseases: an official publication of the Infectious Diseases Society of America. Aug. 1, 2015; 61(3):453-463.
35. Martin A S, Gomez A I, Garcia-Berrocal B, et al. Dose reduction of efavirenz: an observational study describing cost-effectiveness, pharmacokinetics and pharmacogenetics. Pharmacogenomics. May 2014; 15(7):997-1006.
36. Yang S-P, Liu W-C, Lee K-Y, et al. Effectiveness of a reduced dose of efavirenz plus 2 NRTIs as maintenance antiretroviral therapy with the guidance of therapeutic drug monitoring. Journal of the International AIDS Society. Nov. 2, 2014; 17(4Suppl 3):19524.
37. Mochalin V, Osswald S, Gogotsi Y. Contribution of Functional Groups to the Raman Spectrum of Nanodiamond Powders. Chemistry of Materials. 2009 Jan. 27, 2009; 21(2):273-279.
38. Mochalin V N, Pentecost A, Li X-M, et al. Adsorption of Drugs on Nanodiamond: Toward Development of a Drug Delivery Platform. Molecular Pharmaceutics. 2013 Oct. 7, 2013; 10(10):3728-3735.
39. Atluri V S, Kanthikeel S P, Reddy P V, Yndart A, Nair M P. Human synaptic plasticity gene expression profile and dendritic spine density changes in HIV-infected human CNS cells: role in HIV-associated neurocognitive disorders (HAND). PloS one. 2013; 8(4):e61399.
40. Atluri V S, Pilakka-Kanthikeel S, Samikkannu T, et al. Vorinostat positively regulates synaptic plasticity genes expression and spine density in HIV infected neurons: role of nicotine in progression of HIV-associated neurocognitive disorder. Molecular brain. 2014; 7:37.
41. Song P, Yu Y, Wu Q, Fu S. Facile fabrication of HDPE-g-MA/nanodiamond nanocomposites via one-step reactive blending. Nanoscale Res Lett. 2012; 7(1):355.
42. Osswald S, Yushin G, Mochalin V, Kucheyev S O, Gogotsi Y. Control of sp2/sp3 Carbon Ratio and Surface Chemistry of Nanodiamond Powders by Selective Oxidation in Air. Journal of the American Chemical Society. 2006 Sep. 1, 2006; 128(35):11635-11642.
43. P H-A. ESRF Internal Report ESRF97HA02T; ESRF: Grenoble, France. 1997.
44. Huang J, Gautam N, Bathena S P, et al. UPLC-MS/MS quantification of nanoformulated ritonavir, indinavir, atazanavir, and efavirenz in mouse serum and tissues. Journal of chromatography. B, Analytical technologies in the biomedical and life sciences. Aug. 1, 2011; 879(23):2332-2338.
45. Roy U, Atluri V S, Agudelo M, Yndart A, Huang Z, Nair M. D J 1 expression downregulates in neuroblastoma cells (SK-N-MC) chronically exposed to HIV-1 and cocaine. Frontiers in microbiology. 2015; 6:749.
46. Roy U, Ding H, Pilakka-Kanthikeel S, et al. Preparation and characterization of anti-HIV nanodrug targeted to microfold cell of gut-associated lymphoid tissue. International journal of nanomedicine. 2015; 10:5819-5835.
47. Roy U, Bulot C, Honer zu Bentrup K, Mondal D. Specific increase in MDR1 mediated drug-efflux in human brain endothelial cells following co-exposure to HIV-1 and saquinavir. PloS one. 2013; 8(10):e75374.
48. Saiyed Z M, Gandhi N H, Nair M P. Magnetic nanoformulation of azidothymidine 5'-triphosphate for targeted delivery across the blood-brain barrier. International journal of nanomedicine. 2010; 5:157-166.

We claim:

1. A pharmaceutical composition, comprising a plurality of nanodiamond (ND) particles that are less than 10 nm in diameter, each ND particle having a surface with drug molecules adsorbed thereon, and the ND particles can pass through the blood brain barrier of a subject, characterized in that the drug is Efavirenz (EFV).

2. The composition according to claim 1, characterized in that the surfaces of the ND particles are modified with at least one functional group selected from carboxyls, lactones, ketones, ethers, hydroxyls, and amines.

3. The composition according to claim 1, characterized in that the surfaces of the ND particles are modified with at least one biological moiety selected from amino acids, proteins, antibodies, cells, hormones, vitamins, DNA, siRNA, and RNA.

4. The composition according to claim 1, characterized in that the ND particles have an electrostatic charge.

5. The composition according to claim 1, characterized in that the subject is a human.

6. The composition according to claim 1, characterized in that the ND particles are between 3 and 8 nm in diameter.

7. A pharmaceutical composition comprising a plurality of nanodiamond (ND) particles having a diameter between 3 nm and 8 nm, each ND particle having a surface having adsorbed thereto Efavirenz (EFV) drug molecules.

8. A method of treating a viral infection, or a condition associated with a viral infection, in a subject, comprising administering, to the subject, a composition of claim 1.

9. The method according to claim 8, characterized in that the surfaces of the ND particles are modified with at least one functional group selected from carboxyls, lactones, ketones, ethers, hydroxyls, and amines.

10. The method according to claim 8, characterized in that the surfaces of the ND particles are modified with at least one biological moiety selected from amino acids, proteins, cells, hormones, vitamins, DNAs, siRNAs, antibodies, and RNAs.

11. The method according to claim 8, characterized in that the ND particles have an electrostatic charge.

12. The method according to claim 8, wherein the viral infection is in a viral reservoir organ selected from the group consisting of the brain, lymphoid tissue, bone marrow, genital tract, and gut-associated lymphoid tissue.

13. The method according to claim 8, wherein the viral infection is a disease of the central nervous system.

14. The method according to claim 13, wherein the viral infection or the condition associated with the viral infection is neuro-AIDS.

15. The method according to claim 8, wherein the subject is a human.

* * * * *